United States Patent
Adair et al.

(10) Patent No.: US 7,524,463 B2
(45) Date of Patent: Apr. 28, 2009

(54) HEATED VOLATILE DISPENSING DEVICE WITH DYE-BASED USE-UP INDICATOR

(75) Inventors: Joel E. Adair, Racine, WI (US); Brian T. Davis, Burlington, WI (US); Gopal P. Ananth, Racine, WI (US); Padma Prabodh Varanasi, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 217 days.

(21) Appl. No.: 11/346,752

(22) Filed: Feb. 3, 2006

(65) Prior Publication Data

US 2007/0181707 A1 Aug. 9, 2007

(51) Int. Cl.
*A62B 7/08* (2006.01)
*A24F 25/00* (2006.01)

(52) U.S. Cl. ......................... 422/125; 239/53
(58) Field of Classification Search ............ 239/53; 422/125

See application file for complete search history.

(56) References Cited

U.S. PATENT DOCUMENTS

| | | | |
|---|---|---|---|
| 2,782,749 A | 2/1957 | Beckett et al. | |
| 3,962,920 A | 6/1976 | Manske | |
| 4,212,153 A | 7/1980 | Kydonieus et al. | |
| 4,293,095 A | 10/1981 | Hamilton et al. | |
| 4,638,340 A * | 1/1987 | Iiyama et al. | 503/204 |
| 4,824,827 A | 4/1989 | Kelly et al. | |
| 4,903,254 A | 2/1990 | Haas | |
| 4,987,849 A | 1/1991 | Sherman | |
| 5,602,804 A | 2/1997 | Haas | |
| 6,524,000 B1 | 2/2003 | Roth | |
| 6,701,864 B2 | 3/2004 | Watson, Jr. et al. | |
| 6,787,108 B2 * | 9/2004 | Ribi | 422/58 |
| 2003/0168521 A1 * | 9/2003 | Skalitzky et al. | 239/57 |
| 2003/0214997 A1 | 11/2003 | Diekmann et al. | |
| 2004/0240324 A1 | 12/2004 | Isbitsky et al. | |
| 2005/0232615 A1 * | 10/2005 | Flashinski | 392/390 |
| 2006/0000922 A1 | 1/2006 | Martens | |

FOREIGN PATENT DOCUMENTS

| | | |
|---|---|---|
| EP | 0 930 488 | 7/1999 |
| JP | 06287537 | 11/1994 |
| WO | WO 2005/118007 | 12/2005 |

OTHER PUBLICATIONS

ISR for PCT/US2007/002832, May 31, 2007, S.C. Johnson, 6 pages of counter-part ISR.

\* cited by examiner

*Primary Examiner*—Elizabeth L McKane
*Assistant Examiner*—Kevin C Joyner

(57) ABSTRACT

Heated volatile dispensers are disclosed that are provided with automated dye-based use-up indicators. Multiple migrateable dyes of different colors are positioned adjacent a porous substrate. Heating of the substrate, such as a slab impregnated with an insect repellent, both causes the impregnated chemical to dispense from the slab and the indicator dyes to migrate to one or more visible positions. One dye migrates to a visible position faster than a dye of a different color. Further heating may cause one or both dyes to change color at a visible position. The dye movement imparts information about the degree of use-up of the impregnating chemical.

16 Claims, 3 Drawing Sheets

HEATED VOLATILE DISPENSING DEVICE WITH DYE-BASED USE-UP INDICATOR

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to indicators that provide information to consumers about the extent of use of consumable air-treatment products. More specifically, it relates to air treatment dispensing devices where a heater causes dispensing of an air treatment chemical and also initiates a use-up cue system that is in the form of a multiple dye indicator.

A variety of prior art devices are known that use heat to dispense air treatment chemicals. For example, it is known that a porous pad, wick, or other substrate can be impregnated or coated with a volatilizable air treatment chemical. When heat is applied to the substrate, the air treatment chemical is dispensed into the air.

In some of these devices a portion of the substrate is dipped into an associated reservoir of the air treatment chemical (typically a mix of solvent and volatile treatment chemical). The porous substrate then acts as a wick that draws the chemical to the heated region, as needed.

The level of the air treatment chemical/solvent mix in the reservoir is typically visible to consumers. Thus, the emptying of the reservoir provides a way for consumers to monitor when more air treatment chemical is needed. However, for some applications it is preferred not to have to use the somewhat bulky storage reservoir. Further, that type of reservoir system may have certain other disadvantages besides size (e.g. cost).

Hence, the art has developed a variety of porous materials that are impregnated at a factory with air treatment chemicals. They are then positioned adjacent to or on a heater, and the heating dispenses the air treatment chemical into the air from the substrate (by vaporization and/or with assistance of a fan or the like). However, the heating of such a substrate does not typically significantly change the appearance of the substrate, particularly when the substrate is a solid rather than a gel.

Thus, producers of such products will often estimate average useful life of such products under normal usage conditions, and note that information on their packaging. However, these substrates may be used with a variety of different types of heaters which heat at different temperatures or in different ways. Even where only a single type of heater is to be used with a particular type of substrate, heater performance may be inconsistent over time.

While estimated averaging of useful life can provide rough guidance regarding useful life, that estimate will not be exact in most cases. As a result some companies prefer to provide useful life information to consumers in a manner that encourages the product to be thrown away somewhat earlier than the average statistical life. This reduces the risk that there will be significant use of the product after the product has become ineffective, albeit at the cost of a somewhat higher level of waste due to disposing of some product which still has some useful life.

Even where information is provided by the manufacturer regarding expected useful life, some consumers will not learn of, or alternatively not apply, that information. Rather, they will assume what an appropriate useful life is or should be, and thus in some cases prematurely throw away the product, and in others use it after its effective life is over. Further, even where the consumer is initially aware of the appropriate assumption for a usage life, they may forget about the need to replace the product until well after the product has become ineffective.

There are a number of automatic use-up cue systems which have been developed and applied in varied contexts which rely on some form of chemical reaction to cause an automatic color or other visible change after use for a specified period. See e.g. U.S. Pat. Nos. 4,987,849 and 6,787,108. However, systems of this type are difficult to reliably apply in a heated environment, particularly where the exact heat conditions that the product will be exposed to is not controllable or predictable. This is particularly important because chemical reactions typically proceed at very different speeds depending on the environmental temperature.

Some other known indicator devices rely on the migration of a dye to a visible position as an indicator of the extent of use. See e.g. U.S. Pat. Nos. 4,212,153, 4,903,254 and 6,701,864. However, these devices typically require consumer intervention to initiate the dye migration, and sometimes require complex structures to control use of the dye. They thereby unnecessarily increase the cost of the indicator and may also reduce the likelihood of consumer acceptance, particularly where the manner of using the product is not conceptually straightforward.

Other patents which exemplify the general status of knowledge in this art include U.S. Pat. Nos. 4,293,095 and 6,524,000.

Thus, there is still a need in the art to have improved use-up cue systems for heated volatile dispensers which do not rely on viewing liquid levels in a reservoir and can adjust for varied heating conditions.

BRIEF SUMMARY OF THE INVENTION

One aspect the invention provides a substrate capable of dispensing a volatile air treatment chemical upon heating of the substrate. A use indicator is associated with the substrate and configured to automatically communicate an extent to which the air treatment chemical has been dispensed from the substrate as the substrate is heated. That use indicator has at least two dyes which have a different color from each other, and a covering configured to restrict migration of the dyes prior to heating of the substrate and to permit migration of the dyes while the substrate is being heated.

Upon a first extent of heating of the substrate, a first of the two dyes can at least in part migrate to a first visible position. Upon a second extent of heating of the substrate thereafter a second of the two dyes can at least in part migrate to a second visible position that is the same or different from the first visible position. The extent to which the two dyes become visible in this manner is indicative of the extent to which the air treatment chemical has been dispensed from the substrate.

In one preferred form the first and second visible positions are different from each other, and the first visible position is closer to the first dye prior to heating of the substrate than the second visible position is with respect to the second dye prior to heating of the substrate. Alternatively, the first visible position at least partially overlaps with the second visible position to thereby define an overlapping visible position. Upon heating of the substrate the overlapping visible position will first be changed to a first color due to migration of the first of said two dyes to that position, and then upon further heating of the substrate thereafter the overlapping visible position will undergo a color change caused by the second of said two dyes mixing with the first of said two dyes at the overlapping visible position. In any event, the first and second visible positions, and the overlapping position, are preferably on a peripheral portion of the substrate (especially its top surface).

In other preferred forms the first and second of the two dyes are separately stored from each other prior to heating the substrate, or are mixed together prior to heating the substrate, and are formed of materials that migrate through the substrate at different speeds upon heating of the substrate, typically because of having different molecular sizes, charges, or other distinguishing characteristics.

As an example, one heat stable migrating dye is methylene blue, which has a blue color. Another heat stable migrating dye has a larger molecular size and is Sanoplast Red, sold by the Clariant Corporation, which has a red color. The dyes are preferably mixed in a solvent to facilitate handling and positioning.

Alternatively, the dyes can be separately stored and migrate to separate visible locations (e.g. to turn one visible circle area yellow to indicate that the slab is nearly used up, and then to later turn another visible circle area red to indicate that the slab is ready to be disposed of).

A peripheral surface of the substrate (e.g. a top of a slab) can also be pre-marked with a symbolic or textual indication which confirms a degree of use-up of the air treatment chemical once at least one of said two dyes reaches adjacent that pre-marked indication. For example, the phrase "Used Up" could appear adjacent a blank circle that when filled with migrating red dye indicates an exhausted product. Alternatively, the migrating dye could cover over or obscure a marking such as "New".

The first dye could be designed to fill a quarter of a circle or a quarter of a rectangle, followed by a second dye completing a half or more of the circle or rectangle. Alternatively, the visible surface of the substrate could have various bars that are sequentially filled in or covered or connected as each subsequent dye arrives.

As another option the device could be provided with a visible circle that is pre-marked on the top surface. Its central portion could be colored first with one color. The changing and expansion of the coloration due to the second dye could then indicate further use.

The substrate may alternatively have a stepped construction. After heating the covering for the first extent, the first of said two dyes can reach an exposed surface of a first (near) step of the substrate before the second of said two dyes reaches an exposed surface of a second (farther away) step of the substrate. Note that if the first dye is placed under the near step it would have less distance to travel to reach an exposed surface than a second dye placed only under the farther away step. Hence, the first dye would become visible on the first step before the second dye becomes visible on the second step, if the substrate is uniformly porous.

The dye could be encapsulated (a "covering") prior to use with a meltable wax or plastic (e.g. ethylene vinyl acetate or polyethylene). Alternatively, it could be stored prior to use in separate cavities under substrate portions having pores that are initially too tiny to permit migration to a visible surface at room temperature. Heating of the substrate can expand the pores and thus permit such migration. Each dye could be stored in a different pore/substrate configuration. In this regard, a nylon 6.6 substrate with larger pores could permit one speed of migration of one dye, and a high density polyethylene substrate with smaller pores could permit a second dye to migrate more slowly.

Another form of the invention provides a device for dispensing an air treatment chemical into a surrounding air environment in response to heating of a substrate. The device has a porous substrate to which has been applied the air treatment chemical, at least two dyes positioned in, against, or adjacent the substrate, and means for controlling migration of the at least two dyes such that migration of the at least two dyes prior to said heating is restricted, and migration of said at least two dyes to visible surface(s) after such heating can occur.

In yet another form the invention provides a method of producing an air treatment device having an automatic use-up indicator. One covers two migrate able dyes having differing color adjacent a porous substrate (e.g. with a meltable wax or expandable pore structure). One also impregnates the substrate with an air treatment chemical.

A wide variety of volatile air treatment chemicals can be dispensed via heated volatile dispensers, as is well known in the art. This may include, for example, insect control actives, fragrances, sanitizers and deodorizers. Particularly preferred insect control actives are insect control repellents and insecticides such as pyrethroids (e.g. transfluthrin or metofluthrin), mixed, if used in a liquid form, with from 99 to 95 wt percent of a suitable, volatile solvent. Hydrocarbon solvents such as Exxon Corporation's Isopar solvents are examples. Alternatively, even solid or gel form air treatment chemicals could be used provided that upon heating they will volatilize.

For example, the device could dispense an insect control repellent. The first dye could be timed to provide a first signal when dispensing has gone on long enough to provide effective protection, and the second dye could be timed to signal when to throw away the substrate.

An especially preferred substrate for this purpose would be a porous heat stable slab-like substrate, such as one of the porous substrates conventionally used for dispensing insect repellents. Examples include, without limitation, sintered ceramics, compressed cellulosic materials, porous polymers, and silica or other particles bound into a mass by a resin material.

Where one or more migrating dyes that are used is not stable under heat and air exposure, the instability can provide additional information to the consumer. For example, the initial migration of one dye might provide one color signal, and a further color change of the dye after it first appears (due to further heating and air exposure) could communicate additional usage. This information can be further augmented by the arrival of a second dye. Consider for example a green migrateable dye that when reaching a visible position gradually turns yellow. That dye might indicate that operation of the device has just begun when the green color first appears, and gradually indicate that the product is becoming used up as the yellow begins to appear. Then, when the second dye appears at a separate position (for example a red), the appearance of the red color could indicate complete use up.

In another form, the invention is a use indicator configured to automatically communicate the extent to which the use indicator has been exposed to a selected use temperature, typically a temperature in excess of common ambient or storage temperatures anticipated to be experienced by the use indicator. The use indicator includes at least two dyes, each having an at least somewhat different color from the other.

A covering is configured to restrict migration of the dyes prior to heating of the covering to the use temperature, and to permit migration of the dyes while heated to the use temperature. Upon a first extent of heating of the use indicator, a first of said two dyes can at least in part migrate to a first visible position. Upon a second extent of heating of the use indicator after the first extent of heating, a second of said two dyes can at least in part migrate to a second visible position that is the same or different from the first visible position. The extent to which the two dyes become visible in this manner is indicative of the total exposure of the use indicator to the use temperature.

The principles of the present invention can be applied using a wide variety of heating devices. The exact nature of the heater is not critical. While electrical heaters are preferred, even flame heaters (e.g. insect control lanterns) can have the principles of the present invention effectively applied to them. In any event, one preferred form of electrical heater that may be used with insect repellent slabs is the insect mat heater sold by S. C. Johnson & Son, Inc. under the Raid® brand.

The present invention thus provides an automatic means of indicating to a consumer the extent to which a consumable portion of air treatment devices have been used up. The substrates of the present invention are inexpensive to produce, reliable, and conceptually straightforward insofar as a consumer's ability to readily understand how they operate. They help avoid waste due to the premature disposal of such consumables even when they still have considerable useful life, and they help reduce consumer dissatisfaction which can be caused by use of a consumable after its effective life is over.

The foregoing and other advantages of the present invention will be apparent from the following description. In that description reference is made to the accompanying drawings which form a part thereof, and in which there is shown by way of illustration, and not limitation, preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

Figure 1:
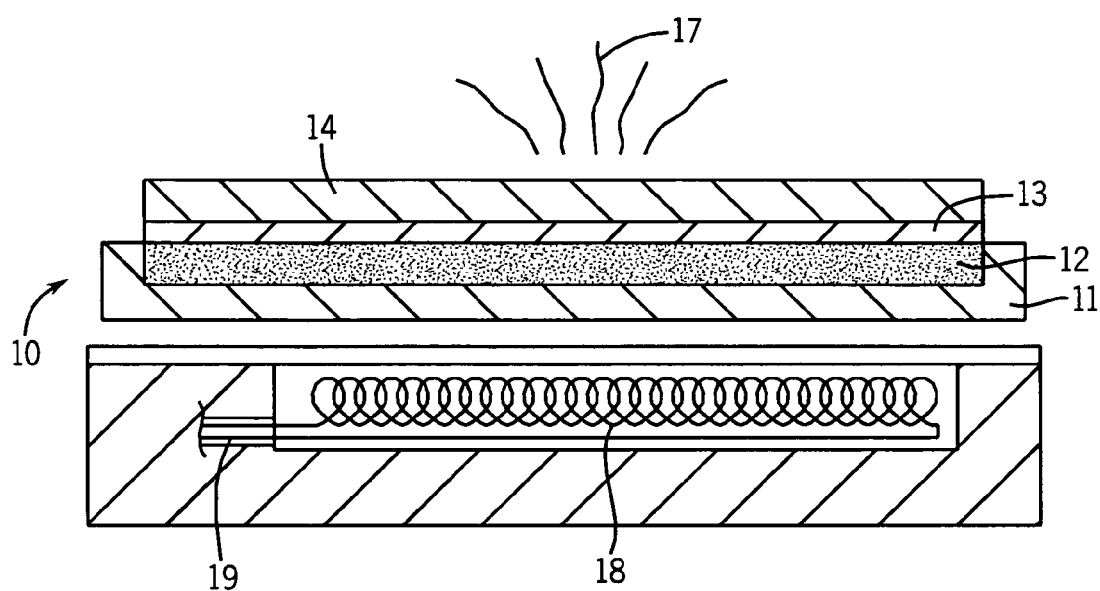
FIG. 1 is a schematic cross-sectional view of an air-treatment device in accordance with the present invention.
Figure 2:
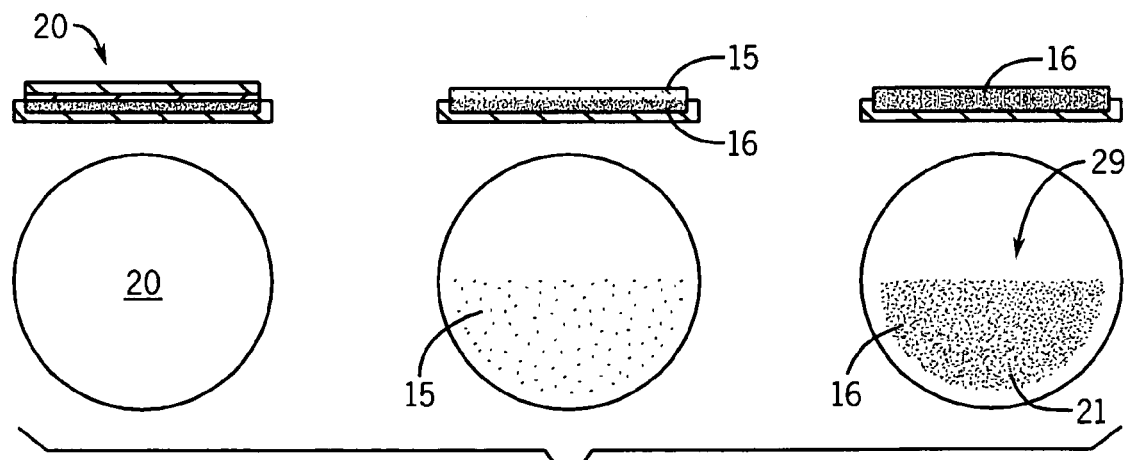
FIG. 2 depicts a set of cross-sectional, and corresponding plan, views of the substrate of FIG. 1, at various stages after heating.

Referring first to FIGS. 1 and 2, there is shown an air treatment device 10 which has a substrate with a base 11, a cavity 12 filled with a mix of multiple migrate able dyes 15/16, a meltable wax covering 13, and a porous substrate layer 14. The base 11 is semi-circular cup-shaped, heat resistant, and impermeable to the dyes. The dye cavity 12 is similarly semi-circular and aligned with both the base 11 and the semi-circular viewing position 29 at the top of the substrate layer 14. The substrate layer 14 is circular in top view. The covering 13 is preferably in the form of a semi-circular top.

The porous substrate layer 14 is preferably pre-impregnated with an insect control repellent 17 which is dispensed to the air as the substrate layer 14 is heated. An electrical heater 18 heats the substrate layer 14 and is powered by a conventional electrical connection 19. When the heater 18 is turned on, one of the effects is to melt the wax of the covering 13. Upon engaging the heater 18, the dyes 15/16 are thereby freed to migrate.

In this embodiment the pores of the porous substrate layer 14 will also expand upon heating. Because one of the dyes 15 in this embodiment has a significantly smaller molecular size than the other dye 16, even after the wax has melted, dye 16 will migrate more slowly than dye 15.

The result of this is schematically depicted in FIG. 2. As shown in the left hand view, no dye has reached the top surface 20 of the porous substrate prior to heating. Heating allows dye 15 to reach the top surface (e.g. a yellow dye—middle view). Further heating allows dye 16 to reach the top surface (e.g. a red dye—right view). Note that in FIG. 2 the dyes are shown as migrating to the same overlapping viewing position 21.

Through appropriate selection of materials and solvents the timing can be coordinated with the timing of the dispensing of the air-treatment chemical. In a preferred form we make our substrate out of either compressed cellulosic materials or silica particles bound into a mass by a resin material, the substrate is impregnated with transfluthrin insect control active ingredient, and the dye mix is a 50-50 mix of methylene blue and Sandoplast Red (Clariant Corporation). This results in an indication of not only that dispensing has begun. It also informs regarding the degree of use.

If desired, the dye can be mixed with additional, or can provide the only, air treatment chemical. However, it is preferred to have the air treatment chemical separately impregnate the substrate outside of the dye cavity.

Figure 3:
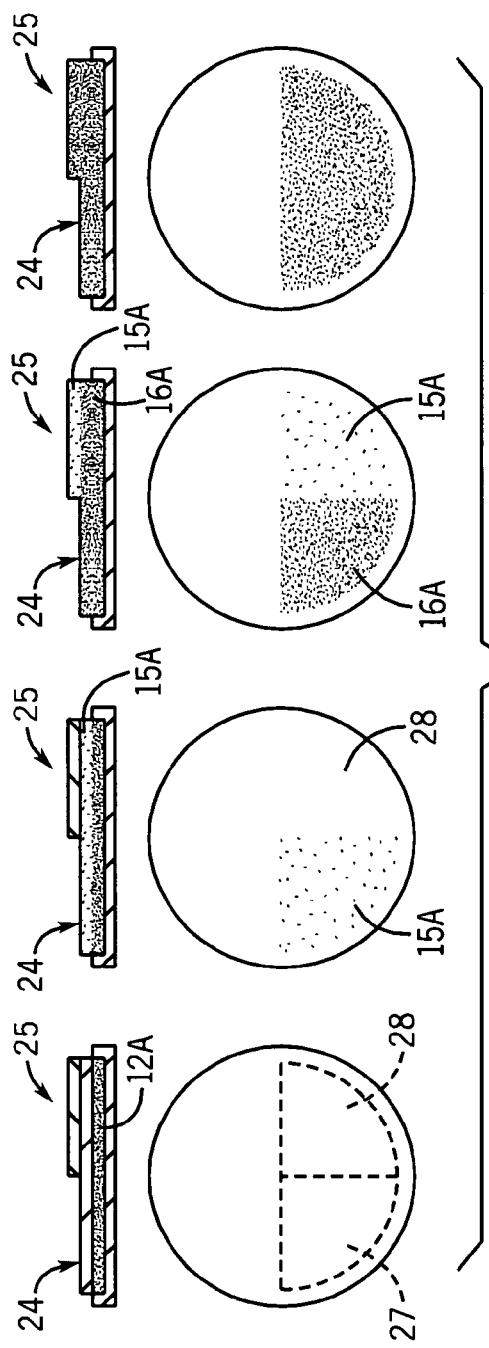
FIG. 3 depicts another set of cross-sectional, and corresponding plan, views of an alternative substrate which could be used with the FIG. 1 heater.

FIG. 3 shows that multiple substrate layers 27/28 may be used to form a stepped structure. Again, expandable pores in the substrate can cause a controlled release of one dye first. Thus, step 24 will color with the first dye first. Then, step 24 will change color to reflect a mixed dying with the second dye, and at this point the first dye will begin to mark the second step 25. Then, the second step will also change color to reflect a mixed dying with the second dye.

This will cause the top view patterns shown in the four views of FIG. 3. The left quadrant 27 will color with the first dye 15A, followed by it changing to reflect the presence of dye 16A. At this point the right quadrant will begin to show color from the first dye 15A. Thereafter, the right quadrant will show the mixed color to indicate complete use-up of the air treatment chemical.

The expandable pores which were described as responsible for this timing could be eliminated if the cavity 12A were bifurcated such that the dye 15A was only under the first step 24 and the dye 16A was only under the second step 25. In such a case the left quadrant 27 would turn color quickly and never change from that color. The right quadrant would later change to the second color.

Figure 4:
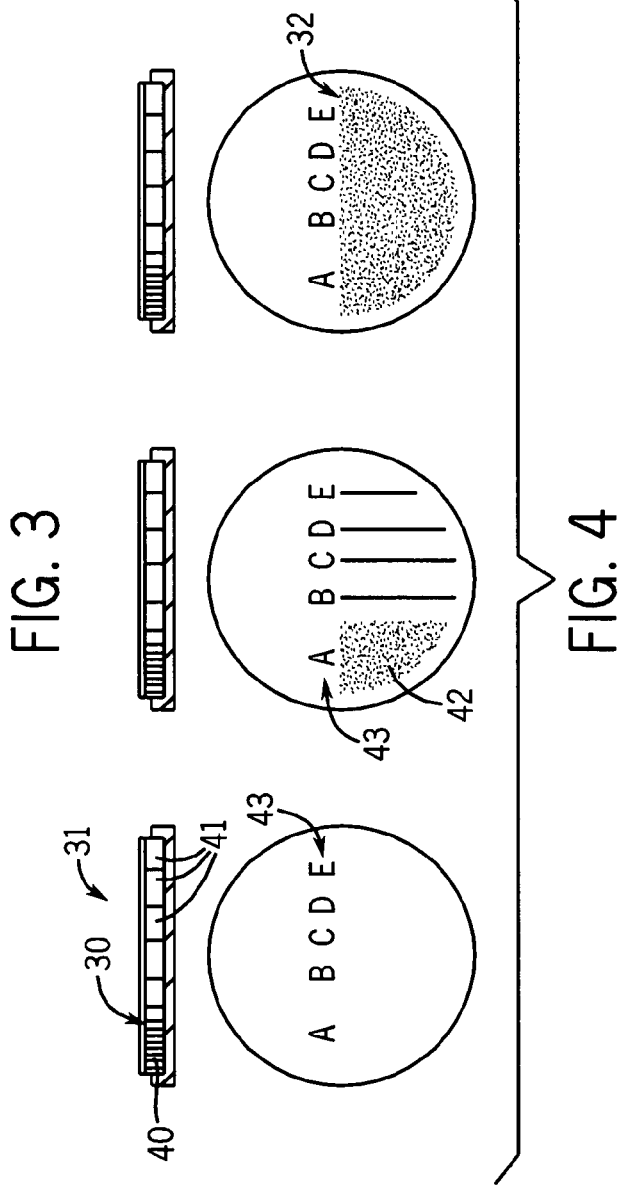
FIG. 4 depicts yet another set of cross-sectional, and corresponding plan, views of an alternative substrate which could be used with the FIG. 1 heater.
Figure 5:
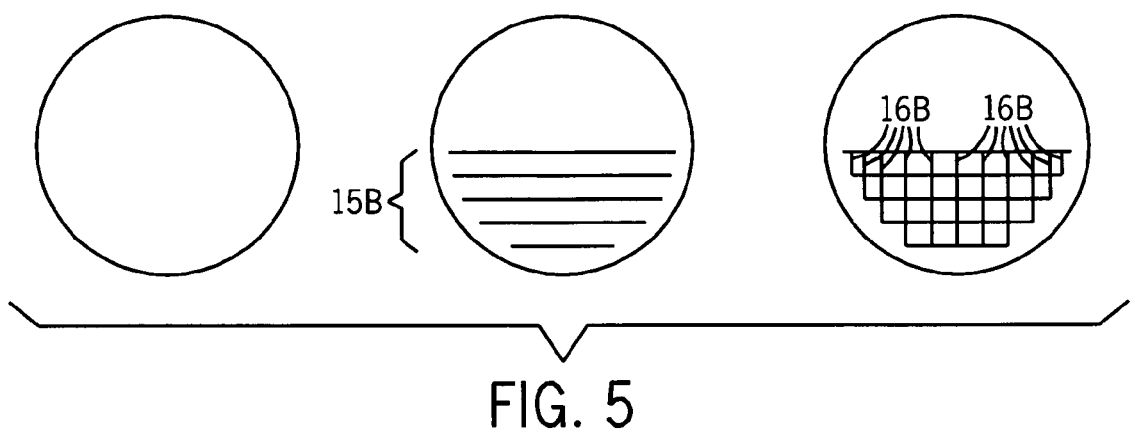
FIG. 5 depicts in schematic form a set of plan views indicating how in another alternative substrate operates.

FIGS. 4 and 5 depict alternative structures where the dyes are stored within aligned passageways 30 prior to heating. These passageways may be narrowed at their upper end so that they do not permit upward migration to visible surface 31 until heating occurs. Then, after heating, those pores expand enough for the dye to migrate first through some of the larger passageways corresponding in FIG. 4 to bars and a region 42.

Further heating causes further expansion of pores, and thus completion of the semi-circle 32.

FIG. 4 shows how some of the passageways with larger diameters can be grouped at a side 40, while others can be spaced at other positions 41. Note that this results in a region 42 being filled first.

Note also the lined designations A, B, C, D and E are permanent markings 43 that provide information regarding the degree of use. One particular color of migrating dye (e.g. green) could be positioned in the pores under region A. The other pores near regions B, C and D could have yellow coloring pre-stored there. Under region E could be stored a third dye, a red.

As shown in FIG. 5, the dyes 15B/16B are arranged under the substrate in grouped sections whereby the first dye 15B is aligned with the substrate in discrete positions. In this regard, a pattern of lines may be formed by the first dye 15B. Similarly, by arranging the second dye 16B in varied discrete positions, the checkerboard pattern can be filled in.

In an analogous manner the first dye could form part of a word, and the second dye the remainder, such that a word such as "Used" appears as the product is exhausted. Alternatively, one or both dyes could obscure a marking such as "New" and also create a marking such as "Used" appear.

Figure 6:
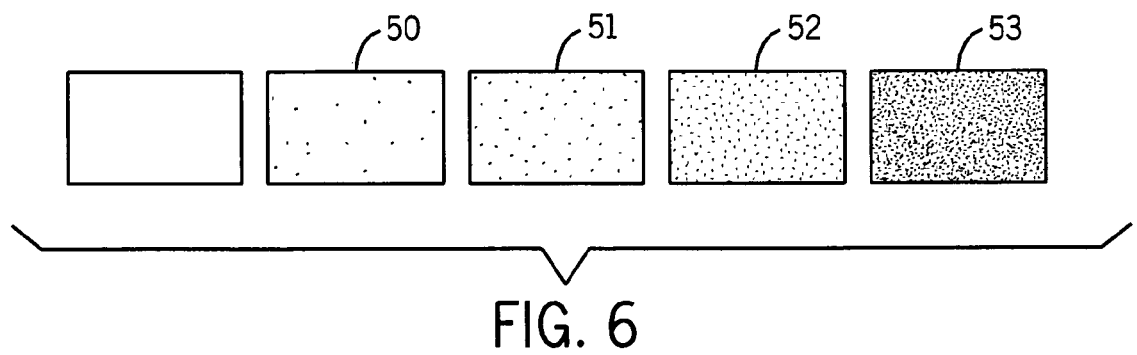
FIG. 6 depicts an alternative embodiment in which a top surface is marked with five rectangles, where four separate supplies feed four of the rectangles with different timing.

FIG. 6 also shows that multiple dyes may be utilized to create a gradient of color feedback. In this design the cavity is divided into five chambers, for of which carry differently colored migrate able dyes. No color would be directly under the leftmost area. One color could be under each of the other four marked regions. The progressive appearance of the colors could indicate the extent of use-up.

As should be appreciated from the examples provided above, the present invention can be applied in a wide variety of ways. For example, the substrates could be square, spherical, or have many other shapes. Thus, the claims should not be construed as being limited to just the disclosed preferred embodiments.

INDUSTRIAL APPLICABILITY

The present invention provides automated use-up cues employing multiple dyes for use with devices that dispense volatile materials in response to heating.

We claim:

1. A substrate capable of dispensing a volatile air treatment chemical upon heating of the substrate in its configuration at a selected use temperature, the substrate comprising:
   said volatile air treatment chemical;
   a use indicator associated with the substrate and configured to automatically communicate an extent to which the air treatment chemical has been dispensed from the substrate as the substrate is heated at the selected use temperature, the use indicator comprising:
      at least two dyes each having an at least somewhat different color from the other; and
      a covering configured to restrict migration of the dyes prior to heating of the covering, and to permit migration of the dyes while the substrate is being heated;
   wherein upon a first extent of heating of the substrate at the selected use temperature, a first of said two dyes can at least in part migrate to a first visible position and be visible;
   wherein upon a second extent of heating of the substrate at the selected use temperature after the first extent of heating a second of said two dyes can at least in part migrate to a second visible position that is the same or different from the first visible position so as to be visible; and
   wherein the extent to which the two dyes become visible in this manner is indicative of the extent to which the air treatment chemical has been dispensed from the substrate.

2. The substrate of claim 1, wherein the first and second visible positions are different from each other, and the first visible position is closer to the first dye prior to heating of the substrate than the second visible position is with respect to the second dye prior to heating of the substrate.

3. The substrate of claim 1, wherein the first and second of said two dyes are separately stored from each other prior to heating the substrate.

4. The substrate of claim 1, wherein the first and second visible positions are on a peripheral portion of the substrate.

5. The substrate of claim 1, wherein the covering comprises a meltable material.

6. The substrate of claim 5, wherein the meltable material comprises a wax.

7. The substrate of claim 1, wherein the substrate comprises pores that expand upon heating of the substrate.

8. The substrate of claim 7, wherein upon heating of the substrate the pores can expand to a size sufficient to allow the first of said two dyes to migrate to the first visible portion while restricting migration of the second of said two dyes.

9. The substrate of claim 8, wherein upon further heating of the substrate the pores will expand still further so as to allow the second of said two dyes to migrate to the second visible portion.

10. The substrate of claim 1, wherein the first and second of said two dyes can upon sufficient heating of the substrate combine to form a pattern that is visible.

11. The substrate of claim 1, wherein a peripheral surface of the substrate is pre-marked with a symbolic or textual indication which indicates a degree of use-up of the air treatment chemical once at least one of said two dyes reaches adjacent that pre-marked indication.

12. The substrate of claim 1, wherein the two dyes have differing molecular sizes from each other.

13. The substrate of claim 1, wherein the substrate has a stepped construction, and, after heating the covering for the first extent, the first of said two dyes can reach an exposed surface of a first step before the second of said two dyes reaches an exposed surface of a second step.

14. The substrate of claim 1, wherein the substrate is a porous solid material that has been impregnated with the air treatment chemical.

15. The substrate of claim 14, wherein the air treatment chemical is selected from the group consisting of insect control actives, fragrances, sanitizers and deodorizers.

16. The substrate of claim 1, wherein after such a dye reaches a visible position, further heating of the substrate will cause the dye to change color.

* * * * *